United States Patent
Mo et al.

(10) Patent No.: US 9,944,577 B2
(45) Date of Patent: Apr. 17, 2018

(54) HYDROQUINONE COMPOUNDS FOR INHIBITING MONOMER POLYMERIZATION

(71) Applicant: BAKER HUGHES INCORPORATED, Houston, TX (US)

(72) Inventors: Hua Mo, Friendswood, TX (US); Roger D. Metzler, Sugar Land, TX (US)

(73) Assignee: Baker Hughes, a GE company, LLC, Houston, TX (US)

( * ) Notice: Subject to any disclaimer, the term of this patent is extended or adjusted under 35 U.S.C. 154(b) by 45 days.

(21) Appl. No.: 14/337,885

(22) Filed: Jul. 22, 2014

(65) Prior Publication Data
US 2014/0330053 A1    Nov. 6, 2014

Related U.S. Application Data

(63) Continuation-in-part of application No. 13/660,488, filed on Oct. 25, 2012.

(51) Int. Cl.
*C07C 255/00* (2006.01)
*C07C 7/20* (2006.01)
*C08F 2/40* (2006.01)

(52) U.S. Cl.
CPC . *C07C 7/20* (2013.01); *C08F 2/40* (2013.01)

(58) Field of Classification Search
None
See application file for complete search history.

(56) References Cited

U.S. PATENT DOCUMENTS

| | | | |
|---|---|---|---|
| 4,032,547 A | 6/1977 | Bacha et al. | |
| 4,590,301 A | 5/1986 | Lim et al. | |
| 5,128,022 A * | 7/1992 | Reid | C09K 15/18 208/48 AA |
| 5,562,863 A | 10/1996 | Arhancet | |
| 5,616,774 A | 4/1997 | Evans et al. | |
| 6,184,276 B1 | 2/2001 | Ignatz-Hoover | |
| 6,284,936 B2 * | 9/2001 | Shahid | 252/182.29 |
| 6,447,649 B1 | 9/2002 | Arhancet | |
| 6,685,823 B2 * | 2/2004 | Benage | B01D 3/34 203/8 |
| 6,926,820 B2 | 8/2005 | Eldin et al. | |
| 7,651,635 B1 | 1/2010 | Lewis | |
| 7,943,809 B2 | 5/2011 | Benage et al. | |
| 2009/0287013 A1 | 11/2009 | Morrison et al. | |
| 2012/0101295 A1 | 4/2012 | Weyler et al. | |
| 2014/0194559 A1 | 7/2014 | Price et al. | |

FOREIGN PATENT DOCUMENTS

| | | |
|---|---|---|
| JP | 3 197430 B2 | 8/2001 |
| WO | 2012033800 A1 | 3/2012 |

OTHER PUBLICATIONS

Shushunova et al. Polymer Science, Ser. B, 2009, vol. 51, 427-437.*
Lartique-Peyrou, 1996, Journal Chem. Lib. vol. 8, pp. 489.*
Chesnokov et al., "Influence of o-benzoquinone nature on initiation of radical polymerization by the o-benzoquinone-tert-amine system," Russian Chemical Bulletin, Intl. Ed. vol. 50, No. 12, pp. 2366-2371 (2001).
Mo, Hua, "Benzylic Radical Scavenging Process by Quinoid Inhibitors", Dissertation, Rich University, (218 pp.), 2004.
Engel, Paul S., et al., "The reaction of a-phenethyl radicals with 1,4-benzoquinone and 2,6-di-tert-butyl-1,4-benzoquinone", Tetrahedron 66, 8805-8814, 2010.
European Search Report in Appln. 13849430.7 dated Jun. 15, 2016.

* cited by examiner

*Primary Examiner* — Sudhakar Katakam
*Assistant Examiner* — Ana Z Muresan
(74) *Attorney, Agent, or Firm* — Mossman, Kumar & Tyler, P.C.

(57) ABSTRACT

The polymerization of monomers may be at least partially reduced or inhibited by introducing an effective amount of an additive. The additive may be or include at least one hydroquinone, such as but not limited to, 2,6-di-tert-butyl hydroquinone, 2,5 di-tert-butyl hydroquinone, 3,5 di-tert-butyl hydroquinone, 3,5 di-methyl hydroquinone, 3,6 di-tert-butyl hydroquinone, and combinations thereof. The polymerizable monomers may be or include, but are not limited to styrene, butadiene, isoprene, acrylic acid, acrylonitrile, vinyl acetate, and combinations thereof.

8 Claims, No Drawings

HYDROQUINONE COMPOUNDS FOR INHIBITING MONOMER POLYMERIZATION

CROSS REFERENCE TO RELATED APPLICATION

This application is a continuation-in-part application of and claims the benefit of U.S. patent Ser. No. 13/660,488 filed on Oct. 25, 2012; which is incorporated by reference herein in its entirety.

TECHNICAL FIELD

The present invention relates to reducing or inhibiting the polymerization of monomers, and more specifically relates to introducing to the monomers an effective amount of an additive to inhibit their polymerization.

BACKGROUND

Common industrial methods for producing various compounds containing vinyl functionality such as styrene, ethene, butadiene, isoprene, vinyl acetate, (meth)acrylic acid, (meth)acrylates, acrolein, acrylonitrile or vinyl-substituted aromatics, typically include separation and purification processes such as distillation to remove unwanted impurities or byproducts. However, undesired polymerization, especially during monomer purification processes such as distillation, results in loss of the monomer product. Moreover, loss of production due to polymer formation on process equipment continues to cause operating problems for those in the industry. In particular, plugging of distillation column overhead piping and fouling or plugging of condensers has been problematic. Therefore, the industry has sought compositions and methods that are less dangerous to handle, that are effective in multiple phases, and that reduce product losses and production problems.

Consequently, additives, which are referred to either as polymerization inhibitors or as polymerization retarders, are added to the olefinically unsaturated monomers generally as early as during the preparation process. Polymerization inhibitors are, as the name actually states, capable of effectively preventing undesired polymerization. Since the reaction rate of polymerization inhibitors is fast, polymerization inhibitors are consumed within a short time. The polymer content rises quickly thereafter. Polymerization retarders, in contrast, can partially prevent polymerization. The rate of polymerization slowly increases Therefore polymerization is effectively hindered or inhibited for a longer period of time, e.g. 4 hours. Due to slow reaction rate, polymerization retarder consumes significantly more slowly than polymerization inhibitors. In general, polymerization inhibitors are used to inhibit polymerization under normal process conditions; whereas, polymerization retarders are used to decrease polymerization reactions during an abnormal process condition, such as an emergency shutdown. The presence of both polymerization inhibitors and polymerization retarders in monomer production may be justified.

It is well known that undesirable and costly polymerization is a significant problem during the manufacturing of various vinyl monomers, particularly vinyl aromatic compounds (e.g., styrene, alpha-methylstyrene and vinyltoluene). Many kinds of polymerization inhibitors and polymerization retarders have been used in the past to minimize this problem. Examples of polymerization inhibitors that have been used to control polymer formation include alkyl-substituted di-nitro-phenols and nitrosophenols diethylhydroxylamine, phenyl-p-phenylenediamines, tert-butyl catechol, and phenothiazine. However, many of these compounds are difficult to handle, are expensive, and/or are regulated heavily with regards to their environmental effect.

Thus, it would be desirable if new polymerization retarders could be developed to inhibit and/or at least partially inhibit the rate of monomer polymerization and which are also cost effective.

SUMMARY

There is provided, in one form, a method for inhibiting the polymerization of monomers by introducing an effective amount of an additive to at least partially inhibit their polymerization. The additive may be or include at least one hydroquinone, such as but not limited to, 2,6-di-tert-butyl hydroquinone, 2,5 di-tert-butyl hydroquinone, 3,5 di-tert-butyl hydroquinone, 3,5 di-methyl hydroquinone, 3,6 di-tert-butyl hydroquinone, and combinations thereof.

There is further provided in another non-limiting embodiment, where the monomers are present in a fluid, such as but not limited to, a refinery fluid, a petrochemical fluid, and mixtures thereof. The additive may include the hydroquinone(s) mentioned above, as well as at least one benzoquinone, such as but not limited to, 3,5-di-tert-butyl-1,2-benzoquinone (3,5 BQ); 3,5-di-methyl-1,2-benzoquinone; 3,6-di-tert-butyl-1,2-benzoquinone, 2,6-di-tert-butyl-1,4-benzoquinone (2,6 BQ); 2,5-di-tert-butyl-1,4-benzoquinone (2,5 BQ); 4-sec-butyl-2,6-di-tert-butylphenol; and combinations thereof.

In an alternative embodiment, a treated monomer stream is provided. The treated monomer stream may include, but is not limited to, polymerizable monomers, and an additive therein for at least partially inhibiting the polymerization of the monomers within the monomer stream. The additive may be or include at least one hydroquinone, such as but not limited to, 2,6-di-tert-butyl hydroquinone, 2,5 di-tert-butyl hydroquinone, 3,5 di-tert-butyl hydroquinone, 3,5 di-methyl hydroquinone, 3,6 di-tert-butyl hydroquinone, and combinations thereof.

The additive appears to at least partially inhibit the polymerization of the polymerizable monomers over a period of time.

DETAILED DESCRIPTION

It has been discovered that the polymerization of monomers may be at least partially reduced or inhibited by introducing to the monomers an effective amount of an additive. The monomer may be or include, but is not limited to acrylic monomers and/or vinyl monomers; alternatively, the monomers may be or include, but are not limited to styrene, butadiene, isoprene, acrylic acid, vinyl acetate, acrylonitrile, and combinations thereof. The monomers may be present in a fluid, such as but not limited to, a refinery fluid, a petrochemical fluid, and combinations thereof.

Non-limiting examples of where the polymerization of the monomers tends to be problematic within the refinery process or petrochemical process may include, but are not limited to light ends, a primary fractionator, pyrolysis gas, and the like. Refinery fluids are fluids that may be further processed or refined at a refinery, such as a petrochemical fluid. In a non-limiting embodiment, the petrochemical fluid may circulate through a hydrotreater, a distillation tower, and combinations thereof. A non-limiting example of a refinery process may include reducing or preventing the formation of foulants, polymerization of monomers, and combinations thereof. Petrochemical fluids may be or include oilfield fluids, crude oil, production water, and the like.

The additive may include at least one polymerization retarder, a polymerization inhibitor, and combinations thereof. Prevent or inhibit is defined herein to mean that the additive may suppress or reduce the amount of total polymerization. That is, it is not necessary for the polymerization to be entirely prevented for the methods and compositions discussed herein to be considered effective, although complete prevention is a desirable goal.

The additive may be or include at least one hydroquinone, such as but not limited to 2,6-di-tert-butyl hydroquinone, 2,5 di-tert-butyl hydroquinone, 3,5 di-tert-butyl hydroquinone, 3,5 di-methyl hydroquinone, 3,6 di-tert-butyl hydroquinone, and combinations thereof. The additive may include the hydroquinone(s) in an amount ranging from about 0.01 ppm independently to about 10,000 ppm, alternatively from about 1 ppm independently to about 5000 ppm, or from about 1 ppm independently to about 1200 ppm. In a non-limiting embodiment, the additive may include at least one optional to quinone in addition the hydroquinone(s). The additive may include at least 50 vol % independently to about 99.5 vol % of the hydroquinone(s), or from about 80 vol % independently to about 95 vol %. The benzoquinones may be present in the additive in an amount ranging from about 0.5 vol % independently to about 50 vol %, alternatively from about 5 vol % independently to about 20 vol %. However, the additive may include the hydroquinones in the absence of the benzoquinones in another non-limiting embodiment.

In a non-limiting embodiment, the hydroquinone may have the general formula (A):

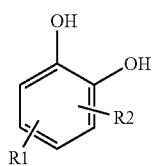

(A)

The benzoquinone may have the general formula (B):

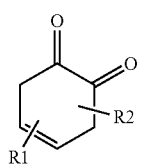

(B)

R1 and R2 may be or include an alkyl group, an aryl group, an alkyl group having a heteroatom, an aryl group having a heteroatom, and combinations thereof. The heteroatom may be or include but is not limited to sulfur, nitrogen, oxygen, and combinations thereof. Non-limiting examples may be or include an ether group, a thiol group, and/or an ester group. The alkyl group of R1 and/or R2 may have from 1 C atom independently to 50 C atoms; alternatively from about 1 C independently to about 20 C atoms. R1 may be the same or different from R2. In one non-limiting embodiment, compound (A) may be 3,5-di-tert-butyl-1,2-benzoquinone (3,5 BQ); 3,5-di-methyl-1,2-benzoquinone, 3,6-di-tert-butyl-1,2-benzoquinone, 2,6-di-tert-butyl-1,4-benzoquinone (2,6 BQ); 2,5-di-tert-butyl-1,4-benzoquinone (2,5 BQ); 4-sec-butyl-2,6-di-tert-butylphenol; and combinations thereof.

The hydroquinones and/or benzoquinones may react with the monomer(s) via thermochemistry, photochemistry, and combinations thereof. As the name suggests, photochemistry requires light to initiate the reaction. Thermochemistry uses heat, instead of light, to initiate the reaction. In a non-limiting embodiment, the hydroquinones and/or benzoquinones may behave differently in the presence of light, which may activate a particular photochemical pathway, and/or heat, which may activate a particular thermochemical pathway. Such reaction mechanisms may be controlled such that the hydroquinones and/or benzoquinones may react via a thermochemical pathway and not a photochemical pathway or vice versa, i.e. the hydroquinones and/or benzoquinones may react via a photochemical pathway and not a thermochemical pathway.

The hydroquinones and the benzoquinones may be classified as 'polymerization retarders' for purposes of the methods described. As used herein with respect to a range, "independently" means that any lower threshold may be used together with any upper threshold to give a suitable alternative range. The hydroquinones and/or the benzoquinones may at least partially inhibit or reduce the rate of polymerization of the monomers for about 0.25 hours independently to about 4 hours, alternatively from about 0.25 hours independently to about 3 hours, or from about 0.5 hours independently to about 2 hours.

The methods described are considered successful if the additive inhibits more of the monomer polymerization than would occur in the absence of the additive. Alternatively, success is obtained if a majority of the monomer polymerization is at least partially inhibited, from about 90% independently to about 99.9%, or from about 96% independently to about 99% in another non-limiting embodiment.

The additive may include a known polymerization inhibitor, such as but not limited to a nitroxide, a hydroxylamine, quinone methide, phenylenediamine derivatives, a hindered phenol, and combinations thereof. The additive may include the polymerization inhibitor in an amount ranging from about 0.01 ppm independently to about 20,000 ppm, alternatively from about 1 ppm independently to about 10,000 ppm, or from about 10 ppm independently to about 1,000 ppm in another non-limiting embodiment. The nitroxide may be or include 2,2,6,6-tetramethyl-1-piperidinyloxyl (TEMPO); 4-HTEMPO; 4-OXOTEMPO; 1-oxyl-2,2,6,6-tetramethylpiperidine, 1-oxyl-2,2,6,6-tetramethypiperidin-4-one, 1-oxyl-2,2,6,6-tetramethylpiperidin-4-yl-2-acetate, 1-oxyl-2,2,6,6tetramethyl-1-piperidin-4-yl-2-ethylhexanoate, and combinations thereof.

The hydroxylamine may be or include hydroxylamines substituted with at least one alkyl, aryl or alkylaryl group include, but are not necessarily limited to N-ethylhydroxylamine (EHA); N,N'diethylhydroxylamine (DEHA); N-ethyl-N-35 methylhydroxylamine (EMHA), N-isopropylhydroxylamine (IPHA); N,N'dibutylhydroxylamine (DBHA); N-amylhydroxylamine (AHA); N-phenylhydroxylamine (PHA); N, N-bis(2-hydroxypropyl)hydroxylamine (HPHA); (N, N-diethylhydroxylamine) (DEHA); and combinations thereof.

The phenylene diamine may be substituted with at least one alkyl group, aryl group, alkylaryl group, and combinations thereof. Non-limiting examples of phenylenediamine derivatives that may be used include, but are not limited to N,N'-Di-sec-butyl-p-phenylenediamine, N,N'-Di-phenyl-p-phenylenediamine, N,N-Dimethyl-p-phenylenediamine, N-phenyl-p-phenylenediamine, and combinations thereof.

A non-limiting example of another polymerization inhibitor is compound (1), which has the general formula:

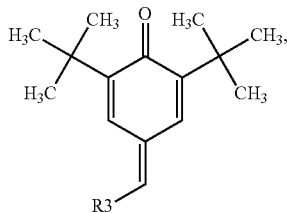

and where R3 may be or include an alkyl group, an aryl group, an alkyl group having a heteroatom, an aryl group having a heteroatom, and combinations thereof. The heteroatom may be or include, but is not limited to sulfur, nitrogen, oxygen, and combinations thereof.

The polymerization inhibitor may be used in conjunction with either the hydroquinone(s), the benzoquinone(s), and combinations thereof, or the polymerization inhibitor may be part of an additive that includes the hydroquinone(s) and/or benzoquinone(s). When the hydroquinone(s) and/or benzoquinone(s) are combined with the polymerization inhibitor, the polymerization of the monomers may be at least temporarily and/or partially inhibited in another non-limiting embodiment. The ratio between the polymerization retarder(s), i.e. either the hydroquinone(s), the benzoquinone(s), and combinations thereof, and the polymerization inhibitor may be based on weight and range from about 1:1 to about 1:10, alternatively from about 1:1 independently to about 1:5. Said differently, the ratio between the hydroquinone and the polymerization inhibitor may be based on weight and range from about 1:1 to about 1:10, alternatively from about 1:1 independently to about 1:5; the ratio between the benzoquinone and the polymerization inhibitor may be based on weight and range from about 1:1 to about 1:10, alternatively from about 1:1 independently to about 1:5; and combinations thereof.

"Additive" is defined herein to be or include a combination of components mentioned below that may be blended together to form a single product for injection into a process stream and/or each individual component to be injected simultaneously into the process. Said differently, two or more components may be added to the process stream at the same time or different times.

Non-limiting combinations of the additive may have or include a benzoquinone and 4-HTEMPO; a benzoquinone and HPHA; a benzoquinone and DEHA; a benzoquinone and HPHA and DEHA; 3,5 tertbutylcatechol (3,5 TBC) and 4-HTEMPO; 3,5 TBC and HPHA; 3,5 TBC and DEHA; 3,5 TBC and HPHA and DEHA; a hydroquinone and 4-HTEMPO; a hydroquinone and HPHA; a benzoquinone and DEHA; a hydroquinone and HPHA and DEHA; and combinations thereof.

The additive may be dispersed in a suitable liquid carrier dispersing medium or alkyl and aromatic solvent, such as but not limited to, heavy aromatic naptha, ethylbenzene, xylene, styrene, paraffinic solvent, and combinations thereof. The amount of the solvent used with the additive may have a ratio based on weight ranging from about a 100:1 ratio independently to about a 2:1 ratio, alternatively from about a 20:1 ratio independently to about a 2:1 ratio.

The additive may be directly added to the monomer stream by direct injection to pump suction or by quill during the distillation, purification, and/or fractionation process. Alternatively, the additive may be added to the equipment used for distillation, purification, and/or fractionation purposes. In one non-limiting embodiment, the additive may be injected into the feed, the reflux, and/or the boiler loop on a continuous basis, or the additive may be injected about every 0.5 hour to about 1 hour in an alternative embodiment.

The invention will be further described with respect to the following Examples which are not meant to limit the invention, but rather to further illustrate the various embodiments.

EXAMPLE 1

A standard gum test was performed where 50 mL of a 25% isoprene in toluene solution was put in a thermo gum glassware for nine different samples. 1 ppm of inhibitor was added in the solution; each sample included a different inhibitor. Sample 1 included 4-hydroxy-2,2,6,6-tetramethylpiperidin-1-oxyl (4 Hydroxy TEMPO); Sample 2 included 4-tert-butylcatechol (TBC); Sample 3 included diethylhydroxyl amine (DEHA); Sample 4 included 2,6-di-tert-butyl-1,4-benzoquinone (2,6 BQ); Sample 5 included 2,5-di-tert-butyl-1,4-benzoquinone (2,5 BQ); Sample 6 included 3,5-di-tert-butyl-1,2-benzoquinone (3,5 BQ); Sample 7 included 2,6-di-t-butyl phenol (Phenol 1); Sample 8 included 2,6-di-tert-butyl-4-sec-butyl phenol (Phenol 2); Sample 9 included 3,5-di-tert-butyl-1,2-hydroquinone (3,5 TBC).

The glassware was put in a pressure vessel, and the pressure was increased to 150 psi with a continuous stream of nitrogen. The pressure vessel was heated to 110° C. for 4 hours. The gum formation was measured by evaporating the unreacted isoprene and toluene with a jet evaporator. The percentage for polymer reduction was measured with the formula:

polymer reduction=(1−gum measurement/blank)× 100.

TABLE 1

Test results at 110° C. (230° F.)

| Sample | Inhibitor | Polymer reduction (%) |
|---|---|---|
| Blank | 0 | 0 |
| 1 | 4HT | 64.42911 |
| 2 | TBC | 43.72647 |
| 3 | DEHA | 46.11041 |
| 4 | 2,6BQ | 41.84442 |
| 5 | 2,5BQ | 33.31242 |
| 6 | 3,5BQ | 49.93726 |
| 7 | Phenol 1 | 36.19824 |
| 8 | Phenol 2 | 26.34881 |
| 9 | 3,5-TBC | 55.83438 |

In the foregoing specification, the invention has been described with reference to specific embodiments thereof, and has been described as effective in providing methods and compositions for at least partially inhibiting the polymerization of monomers by introducing to the monomers an effective amount of an additive. However, it will be evident that various modifications and changes can be made thereto without departing from the broader spirit or scope of the invention as set forth in the appended claims. Accordingly, the specification is to be regarded in an illustrative rather than a restrictive sense. For example, specific monomers, polymerization retarders, polymerization inhibitors, hydroquinones, benzoquinones, and solvents falling within the claimed parameters, and specific proportions or dosages, but not specifically identified or tried in a particular composition or method, are expected to be within the scope of this invention.

The present invention may suitably comprise, consist or consist essentially of the elements disclosed and may be practiced in the absence of an element not disclosed. For instance, the method may consist of or consist essentially of inhibiting the polymerization of monomers by introducing to the monomers an effective amount of an additive, where the additive includes at least at least one hydroquinone selected from the group consisting of 2,6-di-tert-butyl hydroquinone, 2,5 di-tert-butyl hydroquinone, 3,5 di-tert-butyl hydroquinone, 3,5 di-methyl hydroquinone, 3,6 di-tert-butyl hydroquinone, and combinations thereof. The composition may be a treated monomer stream consisting of or consisting essentially of polymerizable monomers, and an additive therein for at least partially inhibiting the polymerization of the monomers within the monomer stream, where the additive includes includes at least at least one hydroquinone selected from the group consisting of 2,6-di-tert-butyl hydroquinone, 2,5 di-tert-butyl hydroquinone, 3,5 di-tert-butyl hydroquinone, 3,5 di-methyl hydroquinone, 3,6 di-tert-butyl hydroquinone, and combinations thereof.

The words "comprising" and "comprises" as used throughout the claims, are to be interpreted to mean "including but not limited to" and "includes but not limited to", respectively.

What is claimed is:

1. A method for inhibiting the polymerization of monomers comprising introducing to the monomers an effective amount of an additive to inhibit the rate of polymerization, wherein the additive consists of:
    a first component selected from the group consisting of 2,6-di-tert-butyl hydroquinone; 3,5 di-tert-butyl hydroquinone; and combinations thereof; and
    a polymerization inhibitor that is a hydroxylamine.

2. The method of claim 1, wherein the ratio between the hydroquinone and the polymerization inhibitor is based on weight and ranges from about a 1:1 ratio to about a 1:10 ratio.

3. The method of claim 1, wherein the effective amount of the additive ranges from about 0.01 ppm to about 10,000 ppm based on the monomers.

4. The method of claim 1, wherein the monomers are selected from the group consisting of styrene, butadiene, isoprene, acrylic acid, acrylonitrile, vinyl acetate, and combinations thereof.

5. The method of claim 1, wherein the monomers are present in a fluid selected from the group consisting of a refinery fluid, a petrochemical fluid, and combinations thereof.

6. A method for inhibiting the polymerization of monomers comprising introducing to the monomers an effective amount of an additive to inhibit the rate of polymerization, wherein the additive consists of:
    a first component selected from the group consisting of 2,6-di-tert-butyl hydroquinone; 3,5 di-tert-butyl hydroquinone; and combinations thereof; and
    a polymerization inhibitor that is a hydroxylamine;
wherein the monomers are selected from the group consisting of styrene, butadiene, isoprene, acrylic acid, acrylonitrile, vinyl acetate, and combinations thereof, and wherein the monomers are present in a fluid selected from the group consisting of a refinery fluid, a petrochemical fluid, and combinations thereof.

7. The method of claim 6, wherein the ratio between the hydroquinone and the polymerization inhibitor is based on weight and ranges from about a 1:1 ratio to about a 1:10 ratio.

8. The method of claim 6, wherein the effective amount of the additive ranges from about 0.01 ppm to about 10,000 ppm based on the monomers.

* * * * *